US012714686B2

(12) United States Patent
Scott et al.

(10) Patent No.: US 12,714,686 B2
(45) Date of Patent: Aug. 25, 2026

(54) N-PROPARGYLGLYCINE: A UNIQUE INHIBITOR OF PROLINE DEHYDROGENASE WITH BRAIN-ENHANCING MITOHORMESIS PROPERTIES CAPABLE OF MITIGATING THE PATHOGENESIS OF NEURODEGENERATIVE DISORDERS

(71) Applicant: Buck Institute for Research on Aging, Novato, CA (US)

(72) Inventors: Gary K. Scott, Berkeley, CA (US); Christopher C. Benz, Petaluma, CA (US); Lisa M. Ellerby, San Anselmo, CA (US)

(73) Assignee: Buck Institute for Research on Aging, Novato, CA (US)

( * ) Notice: Subject to any disclaimer, the term of this patent is extended or adjusted under 35 U.S.C. 154(b) by 652 days.

(21) Appl. No.: 18/250,721

(22) PCT Filed: Oct. 27, 2021

(86) PCT No.: PCT/US2021/072060
§ 371 (c)(1),
(2) Date: Apr. 26, 2023

(87) PCT Pub. No.: WO2022/094565
PCT Pub. Date: May 5, 2022

(65) Prior Publication Data

US 2023/0390232 A1 Dec. 7, 2023

Related U.S. Application Data

(60) Provisional application No. 63/106,814, filed on Oct. 28, 2020.

(51) Int. Cl.

| | |
|---|---|
| ***A61K 31/197*** | (2006.01) |
| ***A61K 9/00*** | (2006.01) |
| ***A61P 25/28*** | (2006.01) |

(52) U.S. Cl.
CPC .......... *A61K 31/197* (2013.01); *A61K 9/0053* (2013.01); *A61P 25/28* (2018.01)

(58) Field of Classification Search
CPC .................................................... A61K 31/197
See application file for complete search history.

(56) References Cited

U.S. PATENT DOCUMENTS

| | | | | |
|---|---|---|---|---|
| 10,322,119 | B2 | 6/2019 | Bassan et al. | |
| 2017/0348266 | A1* | 12/2017 | Scott | G01N 33/57484 |

FOREIGN PATENT DOCUMENTS

| | | | |
|---|---|---|---|
| WO | 2016077632 | A2 | 5/2016 |

OTHER PUBLICATIONS

International Search Report dated May 5, 2022 for related PCT Application No. PCT/US2021/072060, 4 pages.
Written Opinion dated May 5, 2022 for related PCT Application No. PCT/US2021/072060, 6 pages.
Scott, "Targeting mitochondrial proline dehydrogenase with a suicide inhibitor to exploit synthetic lethal interactions with p53 upregulation and glutaminase inhibition", Molecular Cancer Therapy, vol. 18, No. 8, Jun. 12, 2019, 3 pages.
Scott, "N-Propargylglycine: a unique suicide inhibitor of proline dehydrogenase with anticancer activity and brain-enhancing mitohormesis properties", Amino Acids, vol. 53, Jun. 5, 2021, 13 pages.

* cited by examiner

*Primary Examiner* — Rei Tsang Shiao
(74) *Attorney, Agent, or Firm* — Fredrikson & Byron, P.A.

(57) ABSTRACT

In certain embodiments, methods of activating the mitochondrial unfolded protein response (UPRmt) and inducing mitohormesis in the brain and/or central nervous system of a mammal are provided where the methods can involve administering to the mammal an effective amount of N-proparglyglycine (N-PPG). In certain embodiments, the mammal is a mammal with a neurodegenerative disease and the method provides for the treatment or prophylaxis of the neurodegenerative disease.

46 Claims, 11 Drawing Sheets

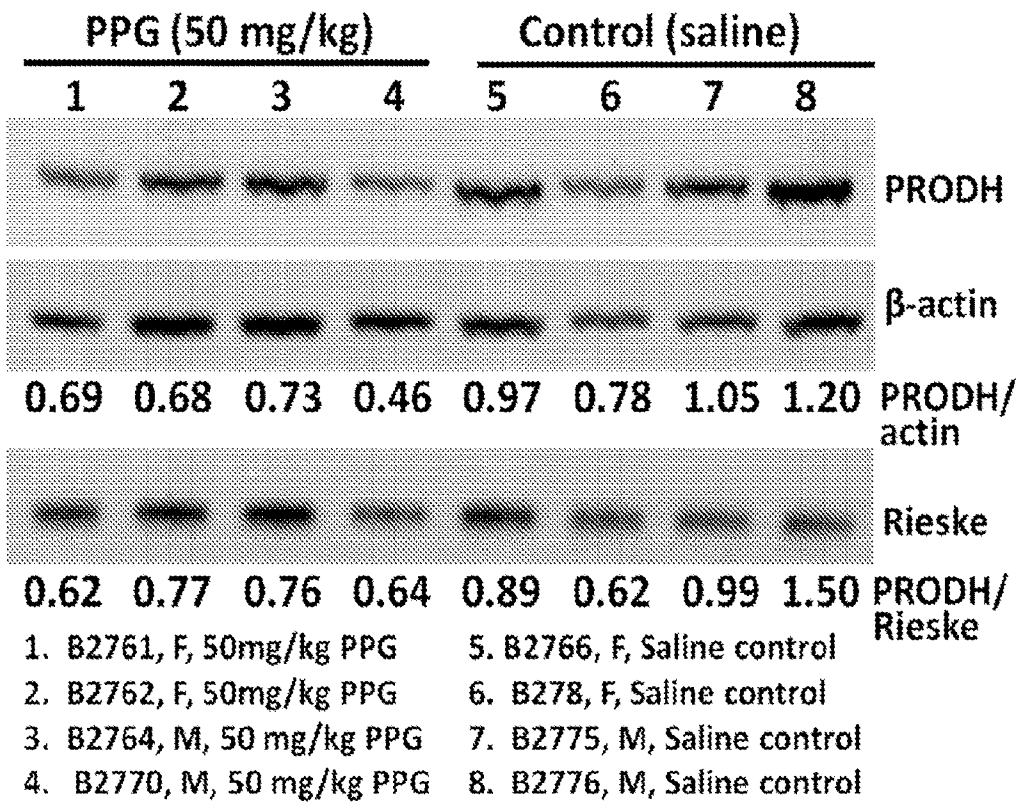
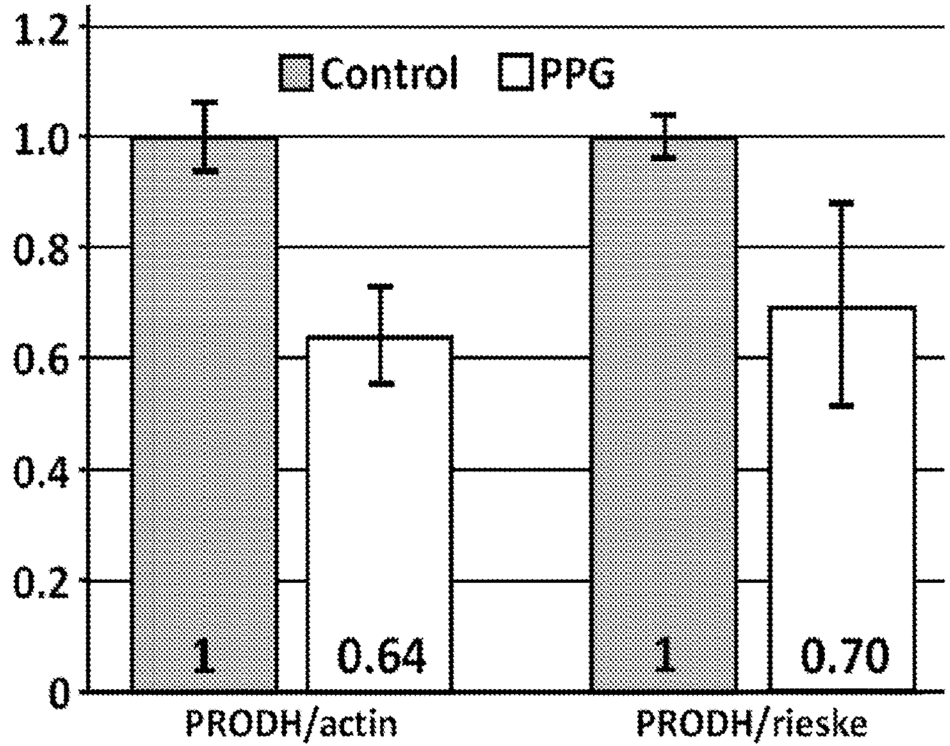
Fig. 1, cont'd.

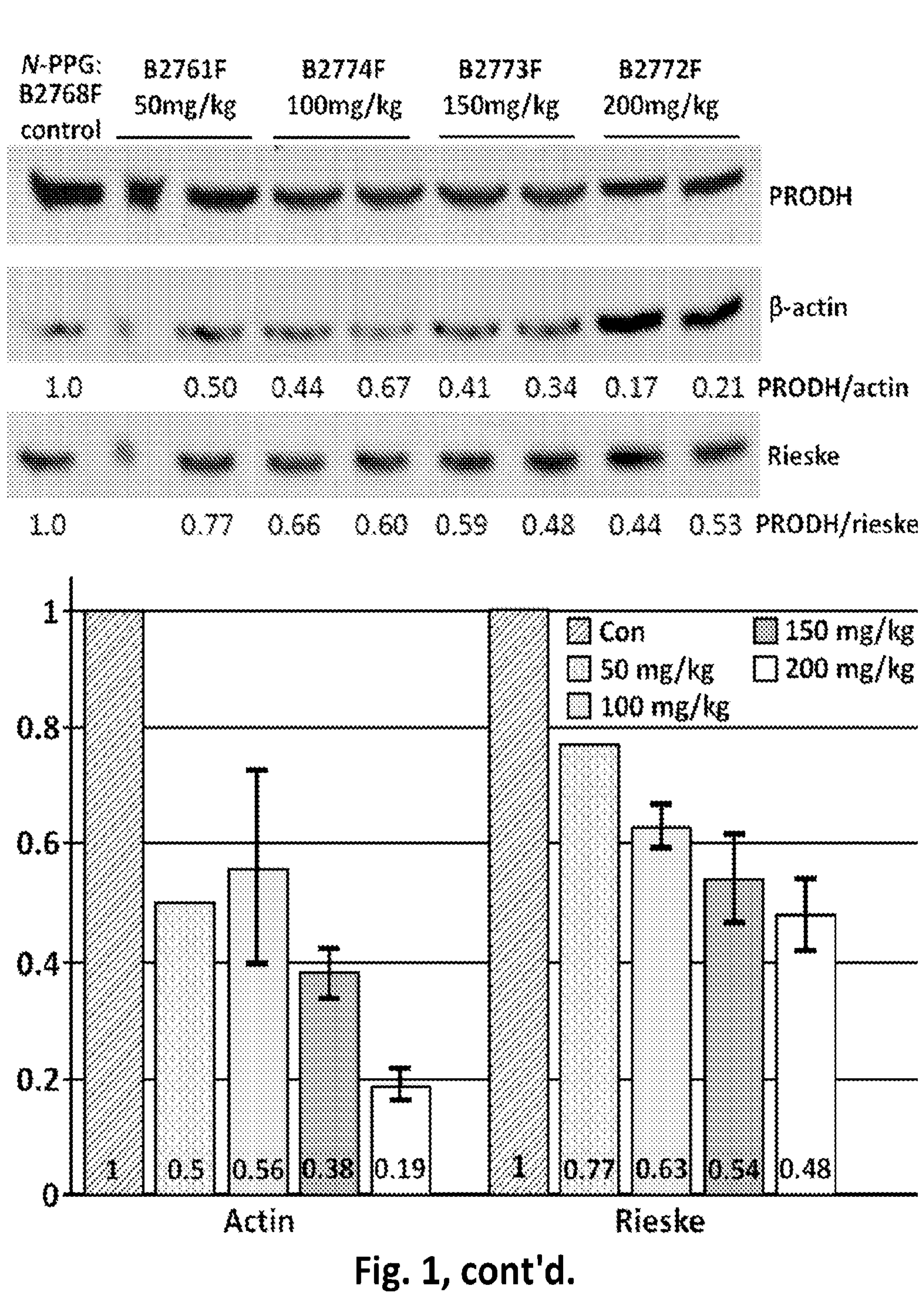
Fig. 1, cont'd.

A

RT-PCR: GAPDH HSP60

C PPG C PPG

PPG induction: 1.0 1.68

GAPDH β2M YME1L1

C *N*-PPG C *N*-PPG C *N*-PPG 1.0 .95 1.35

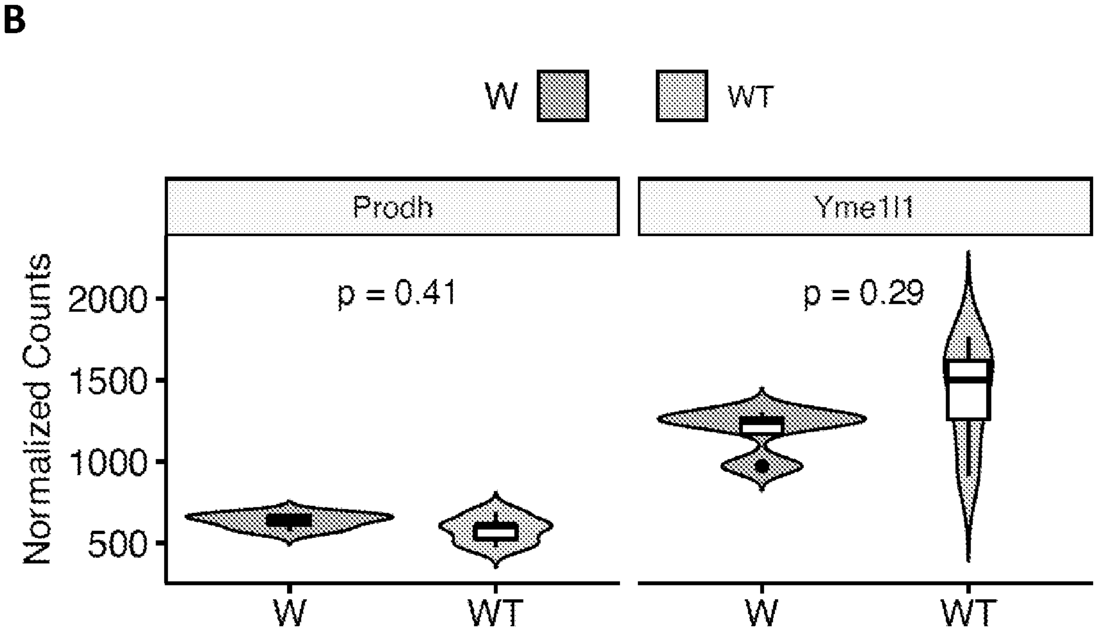
Fig. 2, cont'd.

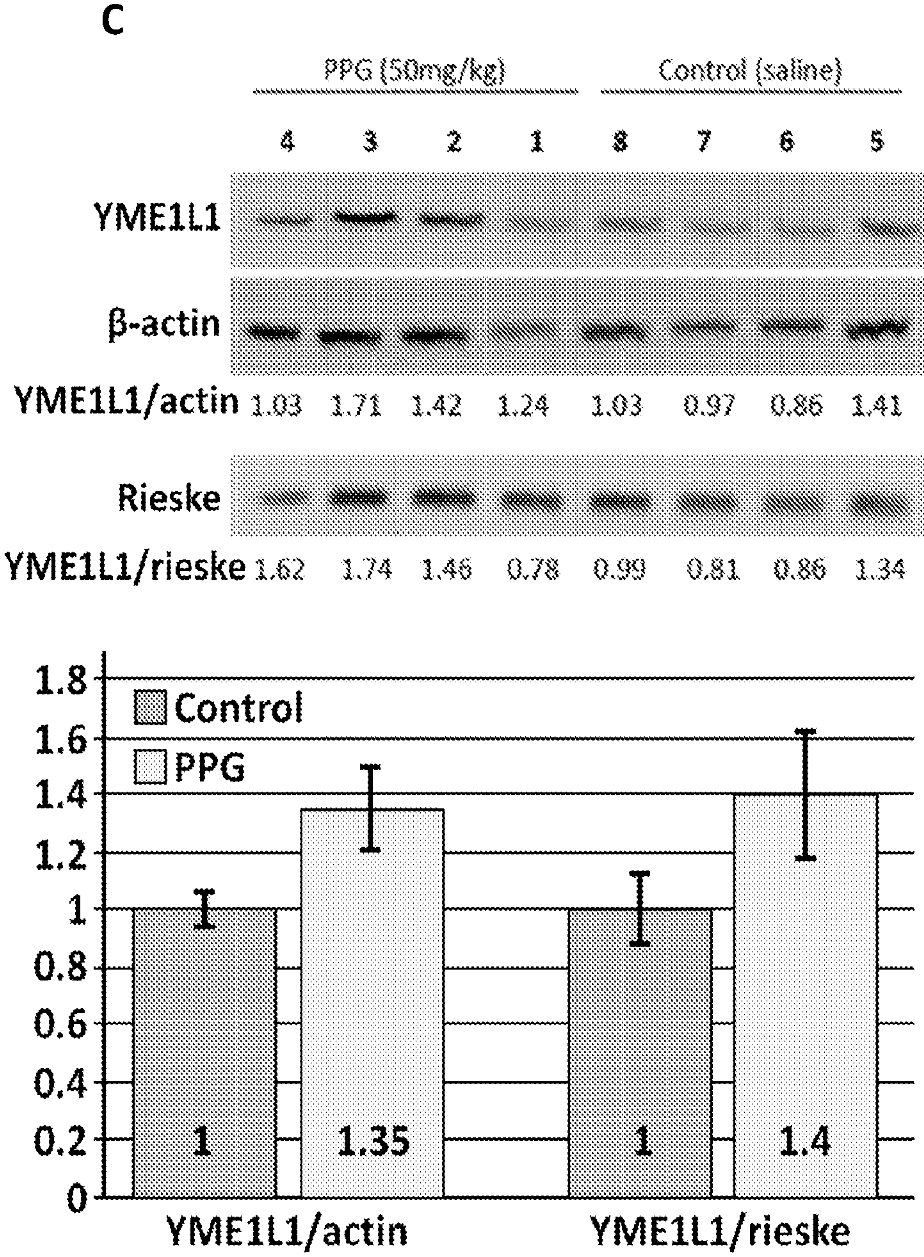
Fig. 2, cont'd.

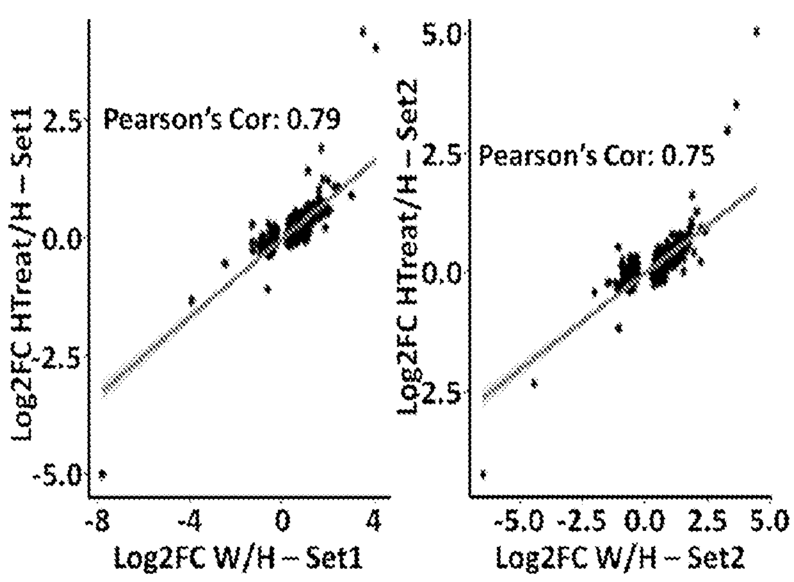

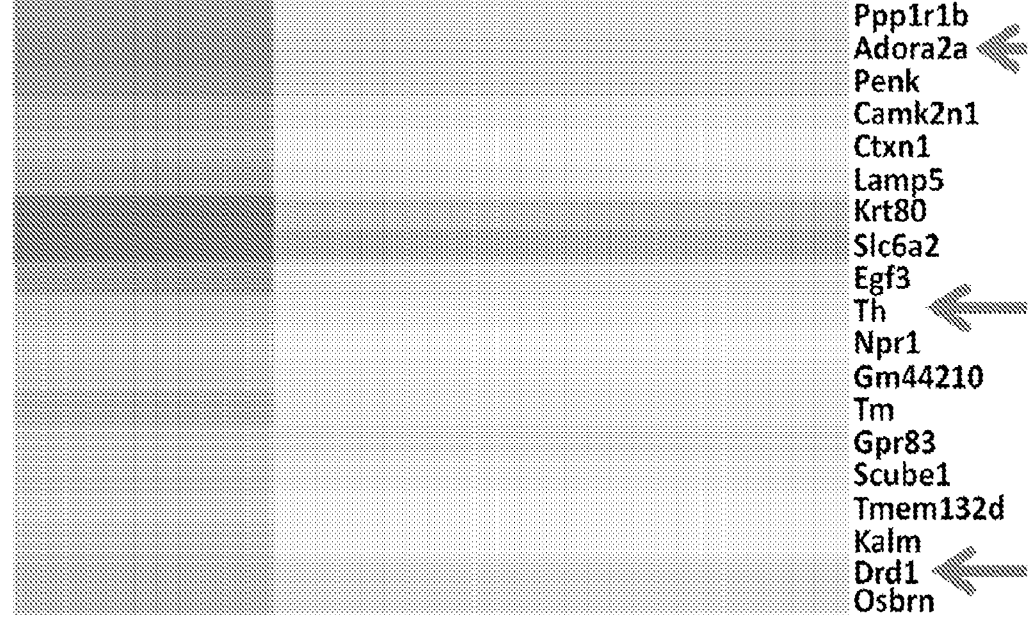

TH: Tyrosine hydroxylase, the rate limiting step in dopamine synthesis is upregulated by PPG to 46% of wild type levels Drd1: Dopamine receptor 1 is upregulated by PPG to 44% of wild type levels ADORA2A: Adenosine A2a Receptor, an important G coupled receptor to increase cyclic AMP levels with dysfunction seen in many neurodegenerative disorders is upregulated by PPG to 32% of wild type levels

Fig. 7

N-PROPARGYLGLYCINE: A UNIQUE INHIBITOR OF PROLINE DEHYDROGENASE WITH BRAIN-ENHANCING MITOHORMESIS PROPERTIES CAPABLE OF MITIGATING THE PATHOGENESIS OF NEURODEGENERATIVE DISORDERS

CROSS-REFERENCE TO RELATED APPLICATIONS

This application claims priority to and benefit of U.S. Ser. No. 63/106,814, filed on Oct. 28, 2020, which is incorporated herein by reference in its entirety for all purposes.

STATEMENT OF GOVERNMENTAL SUPPORT

This invention was made with government support under Grant No. R01-NS100529 awarded by the National Institutes of Health. The Government has certain rights in this invention.

BACKGROUND

Neurodegenerative diseases currently have no effective therapeutics capable of preventing or mitigating their underlying hallmark proteotoxic cellular pathogenesis. Since new therapeutic strategies are desperately needed, it has been suggested that enhancing brain or central nervous system (CNS) mitohormesis, i.e., stressing mitochondria to induce a positive adaptive response, might be a promising approach. However, no target-specific or suitable in vivo mitohormesis-activating drug has yet been identified.

SUMMARY

It was discovered that the mitochondrial enzyme proline dehydrogenase (PRODH) can be targeted with a small molecule suicide inhibitor, N-propargylglycine (N-PPG), that uniquely and irreversibly distorts the enzyme's structure to activate the mitochondrial unfolded protein response ($UPR_{mt}$) and induce mitohormesis in all PRODH expressing mammalian cell systems studied to date. Other known and specific inhibitors of PRODH (e.g., THFA, 5-oxo, T2C) with comparable enzyme inhibiting potency do not activate the $UPR_{mt}$ or induce mitohormesis. While all similarly potent PRODH inhibitors also possess anticancer activity in vitro and in vivo comparable to N-PPG, the unique ability of N-PPG to activate intracellular $UPR_{mt}$ and induce mitohormesis occurs independent of its anticancer activity, consistent with the lack of any local or systemic toxicity when N-PPG is administered at PRODH-inhibiting concentrations to either normal cells or intact mammals.

Accordingly, in certain embodiments, methods of activating the mitochondrial unfolded protein response ($UPR_{mt}$) and inducing mitohormesis in the brain and/or central nervous system of a mammal are provided where the methods comprise administering to the mammal an effective amount of N-proparglyglycine (N-PPG). In certain embodiments, the mammal is a mammal at risk of developing or with established onset of a neurodegenerative disease and the method provides for the treatment or prophylaxis of the neurodegenerative disease.

Additionally, various embodiments contemplated herein may include, but need not be limited to, one or more of the following:

Embodiment 1: A method for the treatment and/or prophylaxis of a neurodegenerative disorder, said method comprising:

administering to a mammal identified as having or as at risk for said neurodegenerative disorder an effective amount of N-propargylglycine (N-PPG).

Embodiment 2: The method of embodiment 1, wherein said neurodegenerative disorder comprises a disorder selected from the group consisting of Huntington's disease, Alzheimer's disease, Parkinson's disease, age-related dementia, mild cognitive impairment (MCI), amyotrophic lateral sclerosis (ALS), and an ischemic event.

Embodiment 3: The method according to any one of embodiments 1-2, wherein said method is for the prophylaxis of said neurodegenerative disorder.

Embodiment 4: The method of embodiment 3, wherein said mammal is a mammal identified as being at elevated risk for said neurodegenerative disorder.

Embodiment 5: The method of embodiment 4, wherein said mammal has a marker for said neurodegenerative disorder.

Embodiment 6: The method of embodiment 5, wherein said neurodegenerative disorder comprises Alzheimer's disease and said marker comprises a marker selected from the group consisting of an ApoE4 allele, a CLR1 gene, and a PLD3 gene, a TREM2 variant, and a SORL1 variant.

Embodiment 7: The method of embodiment 5, wherein said neurodegenerative disorder comprises Alzheimer's disease and said marker comprises a marker selected from the group consisting of a mutant amyloid precursor protein (APP) gene, a mutant presenilin 1 (PSEN1) gene, and a mutant presenilin 2 (PSEN2) gene.

Embodiment 8: The method of embodiment 5, wherein said neurodegenerative disorder comprises Huntington's disease and said marker comprises CAG repeats in the Huntington gene.

Embodiment 9: The method according to any one of embodiments 1-2, wherein said method is for the treatment of said neurodegenerative disorder.

Embodiment 10: The method of embodiment 3, wherein said neurodegenerative disorder comprises Huntington's disease.

Embodiment 11: The method of embodiment 10, wherein said method provides a slowing in the progression of, or a reduction in the magnitude of, or an improvement of a symptom of Huntington's disease.

Embodiment 12: The method of embodiment 11, wherein said method provides a slowing in the progression of, or a reduction in the magnitude of, or an improvement of an indication selected from the group consisting of a Unified Huntington's disease rating scale (UHDS), a motor abnormalities including chorea and/or dystonia, an oculomotor dysfunction, and a problem with gait and balance.

Embodiment 13: The method of embodiment 3, wherein said neurodegenerative disorder comprises Parkinson's disease.

Embodiment 14: The method of embodiment 13, wherein said method provides a slowing in the progression of, or a reduction in the magnitude of, or an improvement of a symptom of Parkinson's disease.

Embodiment 15: The method of embodiment 11, wherein said method provides a slowing in the progression of, or a reduction in the magnitude of, or an improvement of a symptom selected from the group consisting of bradykinesia, resting tremor, and muscle rigidity.

Embodiment 16: The method of embodiment 3, wherein said neurodegenerative disorder comprises Alzheimer's disease.

Embodiment 17: The method of embodiment 16, wherein said method provides a slowing in the progression of, or a reduction in the magnitude of, or an improvement in a symptom of Alzheimer's disease.

Embodiment 18: The method of embodiment 17, wherein said method provides a reduction in the CSF of levels of one or more components selected from the group consisting of Aβ42, sAPPβ, total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, and sAPPα/Aβ42 ratio.

Embodiment 19: The method according to any one of embodiments 17-18, wherein said administration produces a reduction of the plaque load in the brain of the subject.

Embodiment 20: The method according to any one of embodiments 17-19, wherein said administration produces a reduction in the rate of plaque formation in the brain of the subject.

Embodiment 21: The method according to any one of embodiments 17-20, wherein said administration produces an improvement in the cognitive abilities of the subject.

Embodiment 22: The method according to any one of embodiments 17-21, wherein said administration produces an improvement in, a stabilization of, or a reduction in the rate of decline of the clinical dementia rating (CDR) of the subject.

Embodiment 23: The method of embodiment 3, wherein said neurodegenerative disorder comprises age-related dementia and/or mild cognitive impairment (MCI).

Embodiment 24: The method of embodiment 23, wherein said method provides a slowing in the progression of, or a reduction in the magnitude of, or an improvement in a symptom of age-related dementia and/or mild cognitive impairment (MCI).

Embodiment 25: The method of embodiment 24, wherein said method provides an improvement in, a stabilization of, or a reduction in the rate of decline of the clinical dementia rating (CDR) of the subject.

Embodiment 26: The method of embodiment 3, wherein said neurodegenerative disorder comprises amyotrophic lateral sclerosis (ALS).

Embodiment 27: The method of embodiment 26, wherein said method provides a slowing in the progression of, or a reduction in the magnitude of, or an improvement in a symptom of ALS.

Embodiment 28: The method of embodiment 27, wherein said method provides an improvement in, a stabilization of, or a reduction in the rate of decline of muscle strength and/or pulmonary function.

Embodiment 29: The method of embodiment 28, wherein said muscle strength is determined as maximum voluntary isometric contraction. (MVIC), or via hand-held dynamometry (HHD).

Embodiment 30: The method of embodiment 28, wherein said pulmonary function comprise forced vital capacity (FVC) and/or maximal inspiratory pressure (MIP).

Embodiment 31: The method of embodiment 3, wherein said neurodegenerative disorder comprises delayed neurodegeneration following an ischemic event.

Embodiment 32: The method of embodiment 31, wherein said ischemic event is due to stroke or traumatic brain injury.

Embodiment 33: The method of embodiment 32, wherein said method provides an improvement in, a stabilization of, or a reduction in the rate of neurological damage.

Embodiment 34: The method according to any one of embodiments 1-33, wherein said wherein said administering causes specific degradation of mitochondrial PRODH protein.

Embodiment 35: The method according to any one of embodiments 1-34, wherein said administering produce an increase in YME1L1.

Embodiment 36: The method according to any one of embodiments 1-35, wherein said administering upregulates expression of one or more of DRD1, TH, ADORA to normal levels seen in a wildtype mammal without a neurodegenerative disorder.

Embodiment 37: The method according to any one of embodiments 1-36, wherein said administering is at a dosage that produces no adverse side effects associated with downregulation or inhibition of PRODH.

Embodiment 38: The method according to any one of embodiments 1-37, wherein said administering is at a dose that ranges from about 50 mg/kg up to about 200 mg/kg.

Embodiment 39: The method according to any one of embodiments 1-38, wherein said administering has substantially no effect on monamine oxidase B levels.

Embodiment 40: The method according to any one of embodiments 1-39, wherein said administering has substantially no effect on monamine oxidase A levels.

Embodiment 41: The method according to any one of embodiments 1-39, wherein said administering has substantially no effect on monamine oxidase levels.

Embodiment 42: The method according to any one of embodiments 1-41, wherein said mammal is a human.

Embodiment 43: The method according to any one of embodiments 1-41, wherein said mammal is a non-human mammal.

Embodiment 44: The method according to any one of embodiments 1-43, wherein said N-PPG is administered to said mammal human for at one month, or at least two months, or at least 3 months, or at least 4 months, or at least 5 months, or at least 6 months, or at least 1 year.

Embodiment 45: The method according to any one of embodiments 1-44, wherein said N-PPG is an oral formulation that is administered at least once daily.

Embodiment 46: The method according to any one of embodiments 1-45, wherein said mammal is not diagnosed with and/or under treatment for a cancer.

Definitions

The terms "subject," "individual," and "patient" may be used interchangeably and refer to humans, as well as non-human mammals (e.g., non-human primates, canines, equines, felines, porcines, bovines, ungulates, rodents, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for a neurodegenerative disorder as described herein. Thus, for example, in certain embodiments the subject is a subject with Huntington's disease, Parksinon's disease, Alzheimer's disease and the like. In certain embodiments the methods described herein are prophylactic and the subject is one in whom a neurological disorder is to be inhibited/slowed or prevented. In certain embodiments the subject for prophylaxis is one with a family history of a neurodegenerative disorder and/or a risk factor for a neurodegenerative disorder (e.g., a genetic risk factor, an environmental exposure, and the like).

The term "treat" when used with reference to treating, e.g., a pathology or disease refers to the mitigation and/or elimination of one or more symptoms of that pathology or disease, and/or a delay in the progression and/or a reduction in the rate of onset or severity of one or more symptoms of that disorder or disease, and/or the prevention of that pathology or disease. The term "treat" can refer to prophylactic treatment which includes a delay or in the onset or the prevention of the onset of a pathology or disease.

The term "about" or "approximately" as used herein refers to being within an acceptable error range for the particular value as determined by one of ordinary skill in the art, which will depend in part on how the value is measured or determined, i.e. the limitations of the measurement system, e.g., the degree of precision required for a particular purpose, such as a pharmaceutical formulation. For example, "about" can mean within 1 or more than 1 standard deviation, per the practice in the art. Alternatively, "about" can mean a range of ±20%, preferably ±10%, more preferably ±5% and more preferably still ±1% of a given value.

BRIEF DESCRIPTION OF THE DRAWINGS

FIG. 7 shows data from study "B" showing a strong correlation between W/H and HT/H mouse brain gene ratios that indicate N-PPG treatment normalizes HT transcriptomes away from Htt-mut (H) and more toward wildtype (W) mouse brain transcriptomes. This normalization includes three brain genes showing deranged expression.

DETAILED DESCRIPTION

Figure 1:
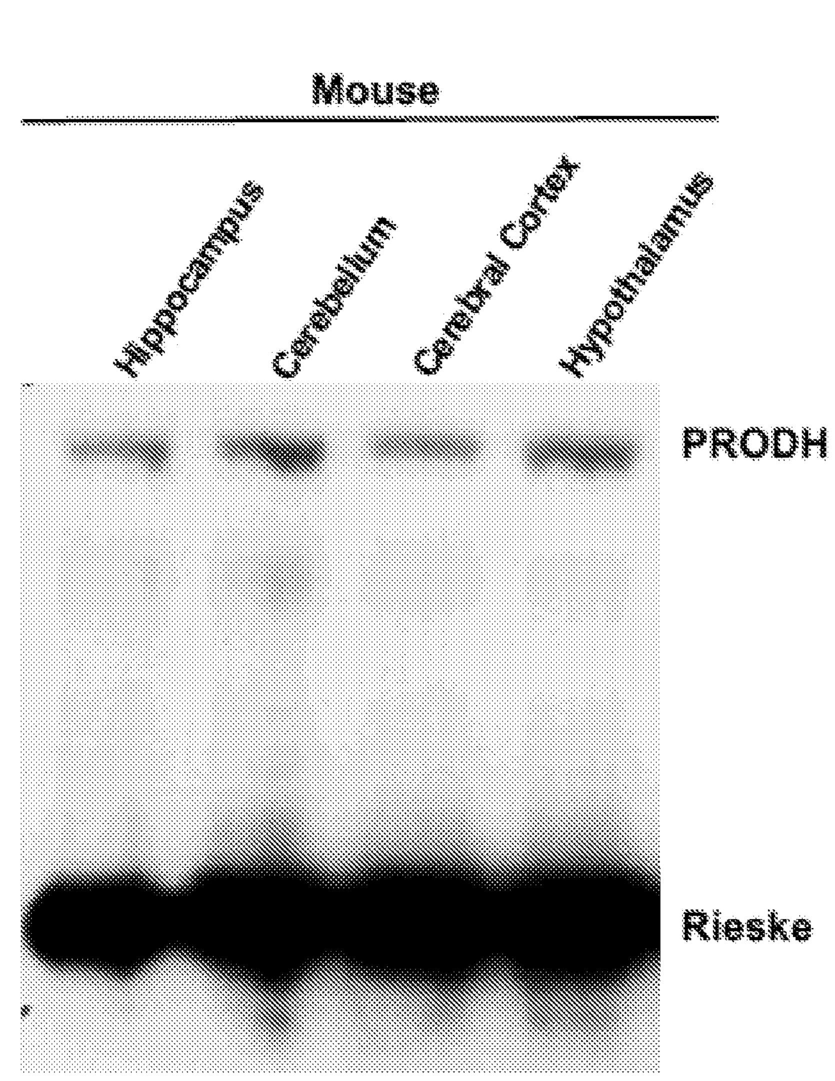
FIG. 1, panels A-C, shows results for study "A" demonstrating that oral N-PPG treatment induces mitochondrial degradation of mouse brain PRODH protein. Panel A) Commercially obtained lysates of indicated mouse brain tissue samples immunoblotted for PRODH protein expression, with total gel protein load normalized to mitochondrial Rieske content. Panel B) Western blots of whole brain lysates from wildtype B6/CBA mice (5 days old) orally treated for nine days with either vehicle (saline) or 50 mg/kg N-PPG (left panel); image analysis quantification of probed PRODH signals normalized to either β-actin or Rieske, with bar graphs of mean ratio values (+/−SD) showing at least 30% reduction in mean PRODH expression following N-PPG treatment (right panel). Panel C) Representative western blot of whole brain lysates, loaded in paired replicates as shown, from five wildtype mice orally treated with saline (control), 50, 100, 150, or 200 mg/kg N-PPG, probed for PRODH, β-actin and Rieske (left side of panel); ratios from blotted technical replicates quantified and bar graphed as described above show dose-dependent decline in normalized mean PRODH expression levels (right side of panel).
Figure 2:
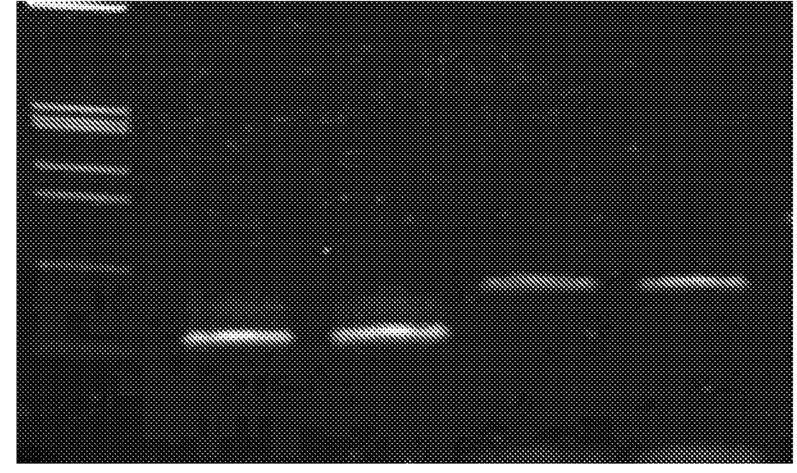
FIG. 2, panels A-C, shows data from study "A" showing that oral N-PPG treatment induces mRNA and protein expression of mouse brain UPRmt protease YME1L1. Panel A) Total RNA extracted from single control (panel C) and 200 mg/kg N-PPG treated mouse brains analyzed by RT-PCR to show 1.7-fold induction of chaperone HSP-60 transcripts and 1.4-fold induction of mitochondrial protease YME1L1 transcripts relative to housekeeping transcripts (GAPDH and 132M) following 9 days of oral N-PPG treatment. Panel B) Violin plots (median: dark line, open box: Q1-Q3, distribution with max./min. values) of PRODH and YME1L1 gene expression values from full RNA sequencing dataset (RNAseq) on brain samples from all control wildtype (W) and 50 mg/kg N-PPG treated (WT) mice. P-values determined by Wilcoxon test. Panel C) Western blots of whole brain protein lysates from wildtype control (saline vehicle) and 50 mg/kg N-PPG treated mice as analyzed in FIG. 3B, with bar graphs showing image analysis quantification of probed YME1L1 signals normalized to either β-actin or Rieske (mean ratio values+/−SD), showing ~40% increase in mean YME1L1 expression following N-PPG treatment.
Figure 2:
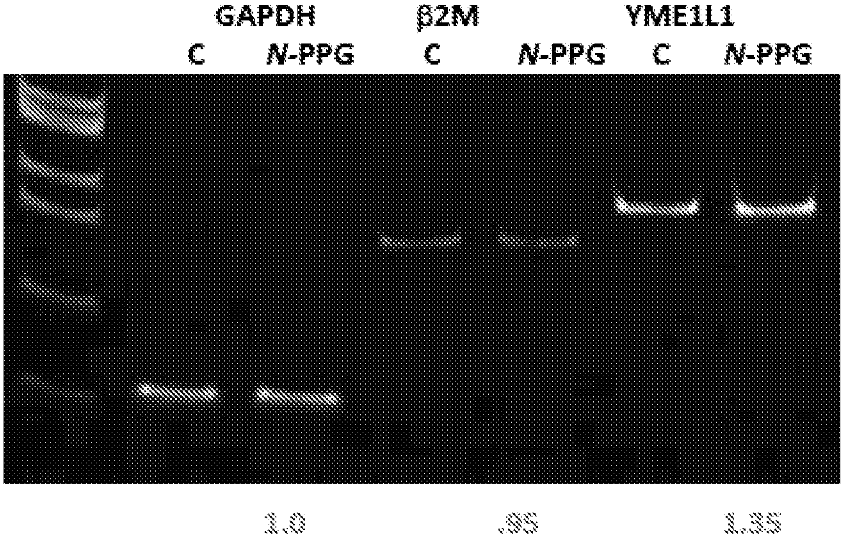
Figure 3:
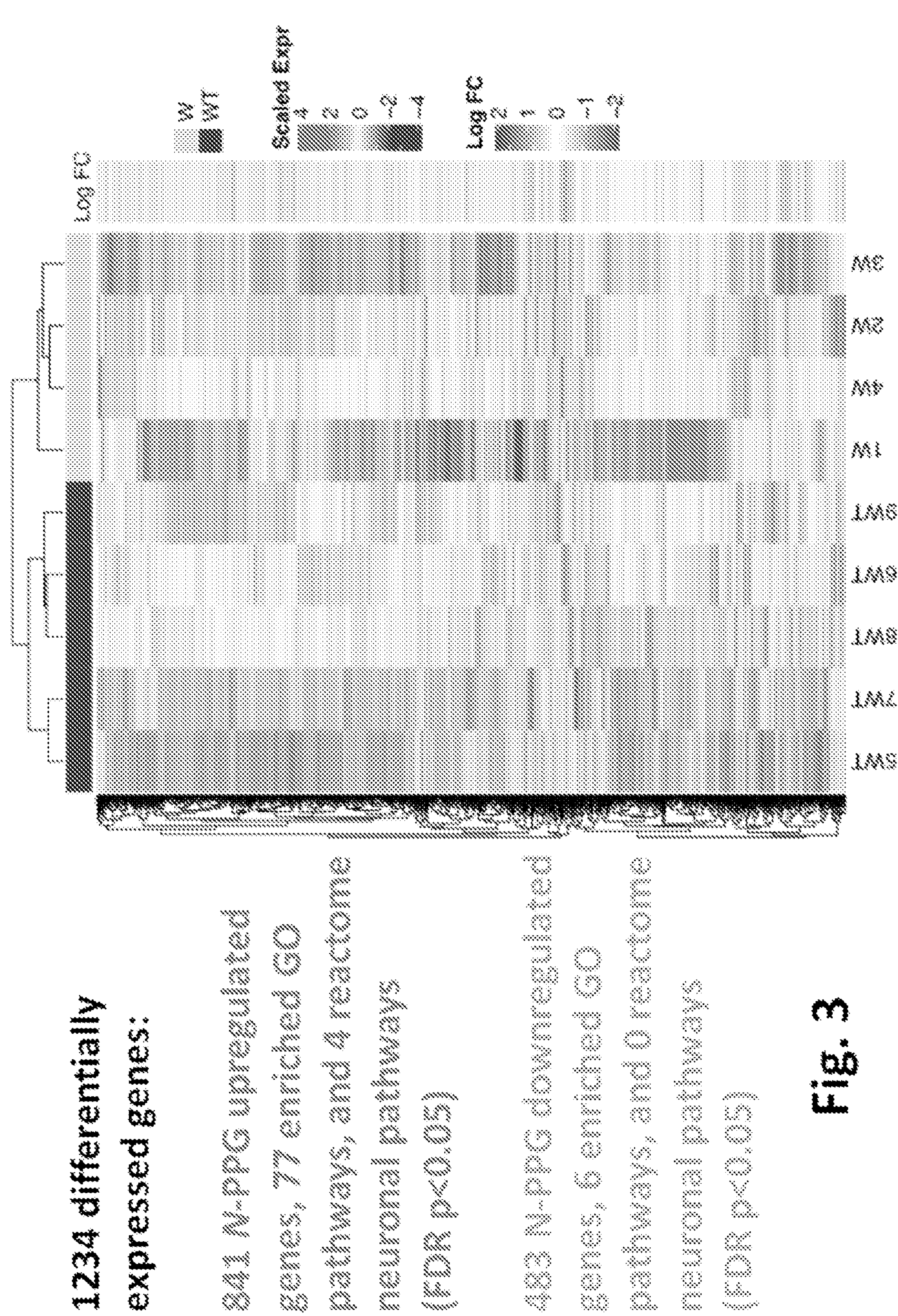
FIG. 3 shows data from study "A" showing transcriptomic (RNAseq) analysis of control (W, wildtype) and N-PPG treated (WT, wildtype treated) mouse brains. Gene expression heat map and unsupervised hierarchical clustering of 1324 genes found to be differentially expressed ($p<0.05$) between five N-PPG treated mouse brains (WT) and four saline treated control brains (W). All WT mice were orally treated for 9 days with 50 mg/kg N-PPG except 5WT who obtained 100 mg/kg N-PPG. Scaled gene expression is shown alongside log-fold changes (Log FC). Upregulated genes (red on heatmap and corresponding green Log FC) include 841 of all 1324 differentially expressed genes, and by over-representation analysis these encode 77 enriched Gene Ontology (GO) pathways and 7 Reactome neural pathways having FDR significance $p<0.05$.
Figure 4:
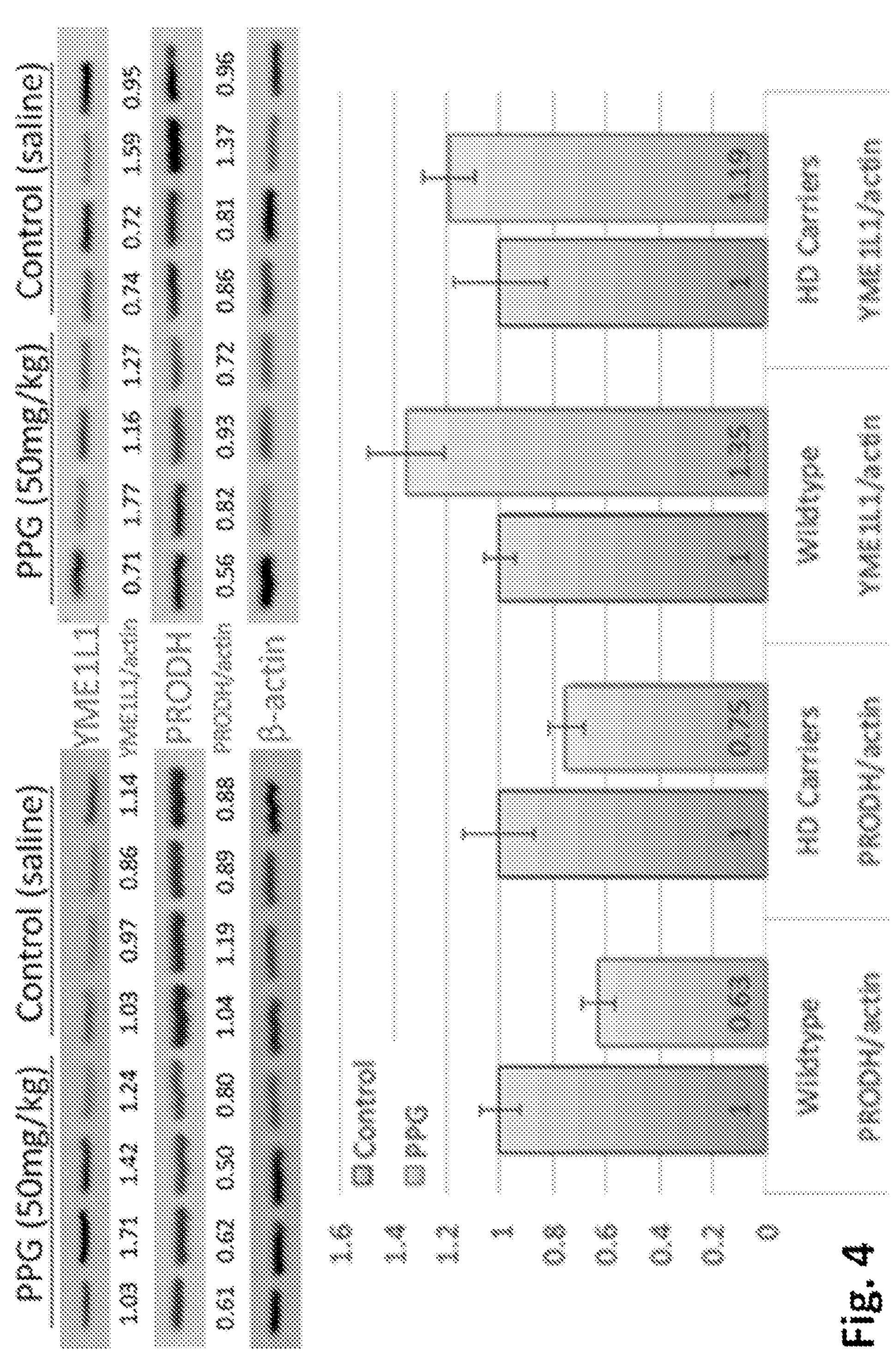
FIG. 4 shows data from study "B" showing that N-PPG treatment produces similar PRODH decay and YME1L1 upregulation in both Htt-mut (HD carrier) and normal (wildtype) mouse brains, signifying comparable $UPR_{mt}$ induction.
Figure 5:
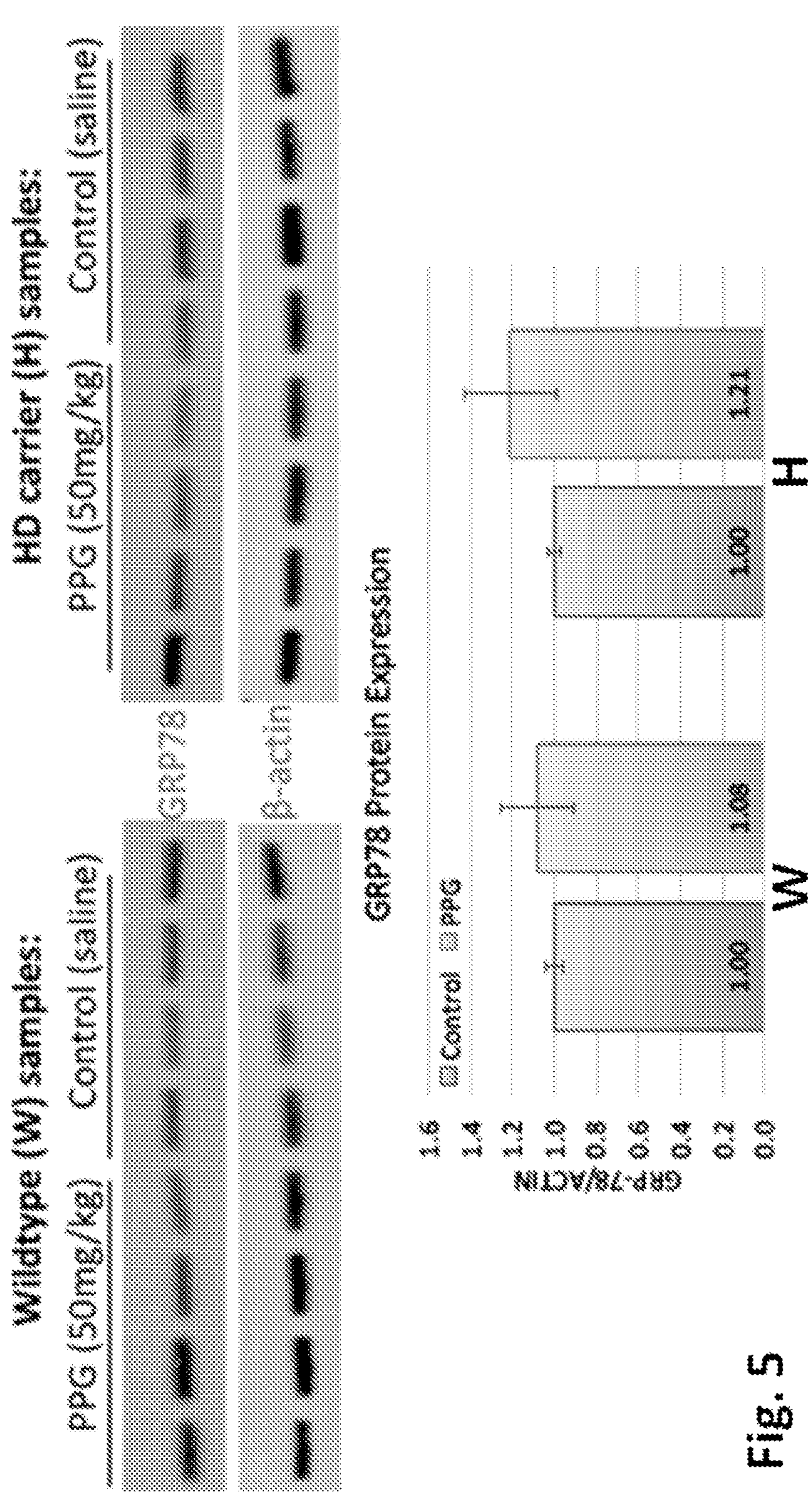
FIG. 5 shows data from study "B" showing that N-PPG treatment produces similar GRP78 chaperone upregulation in both Htt-mut (HD carrier) and normal (W) mouse brains, signifying comparable mitohormesis induction.
Figure 6:
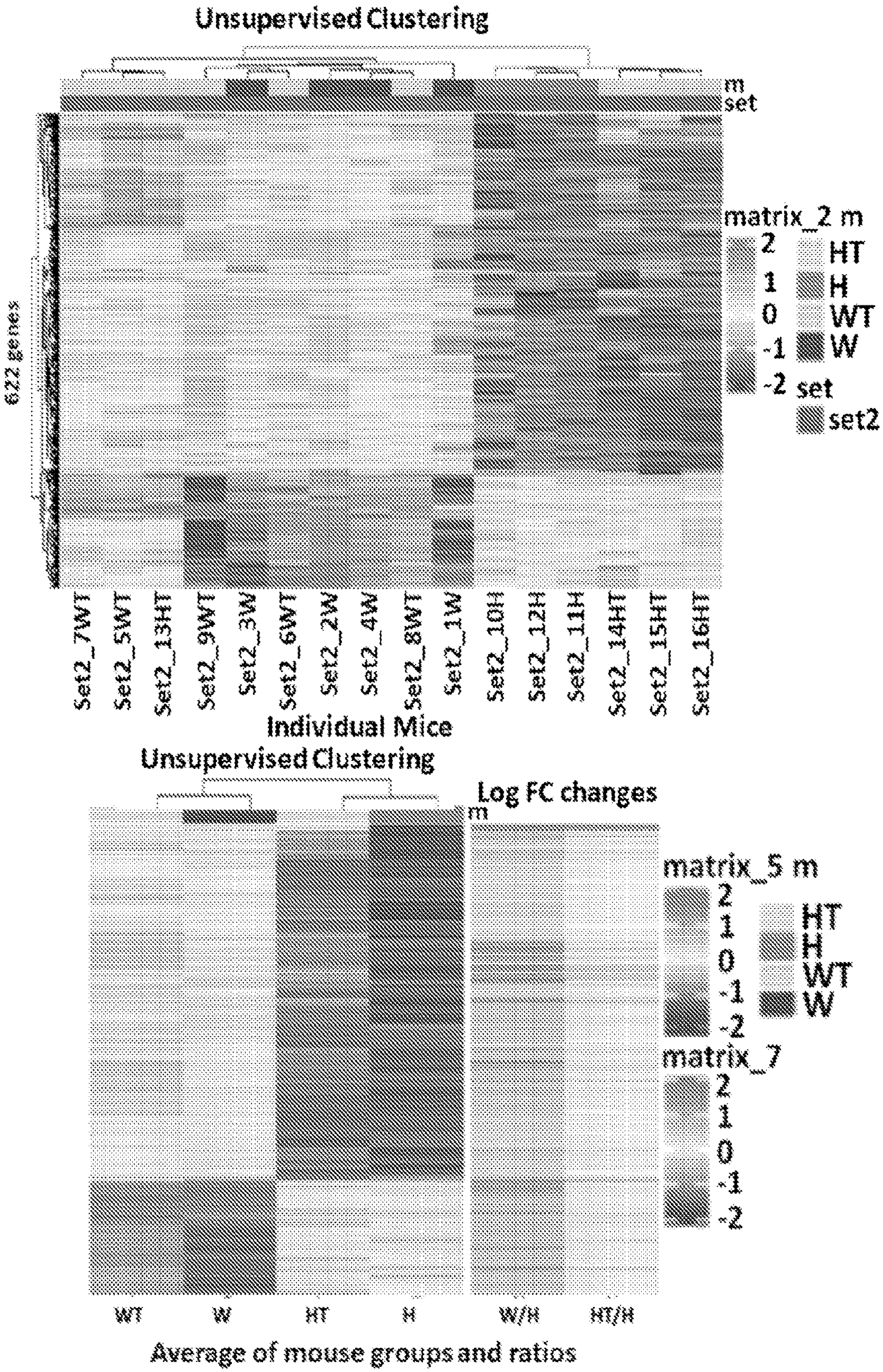
FIG. 6 shows data from study "B" showing comparative expression (622 differentially expressed genes, FDR $p<0.05$) between N-PPG treated wildtype (WT) and Htt-mut mice (HT), untreated wildtype (W) and Htt-mut (H) brains (including the brain transcriptome of Htt-mut mouse #13 fully normalized by N-PPG treatment).

It was discovered that the mitochondrial enzyme proline dehydrogenase (PRODH) can be targeted with a small molecule suicide inhibitor, N-propargylglycine (N-PPG), that uniquely and irreversibly distorts the enzyme's structure to activate the mitochondrial unfolded protein response ($UPR_{mt}$) and induce mitohormesis in all PRODH expressing mammalian cell systems studied to date. Other known and specific inhibitors of PRODH (e.g., THFA, 5-oxo, T2C) with comparable enzyme inhibiting potency do not activate the $UPR_{mt}$ or induce mitohormesis. While all similarly potent PRODH inhibitors also possess anticancer activity in vitro and in vivo comparable to N-PPG, the unique ability of N-PPG to activate intracellular $UPR_{mt}$ and induce mitohormesis occurs independent of its anticancer activity, consistent with the lack of any local or systemic toxicity when N-PPG is administered at PRODH-inhibiting concentrations to either normal cells or intact mammals.

It was a surprising discovery that N-PPG, even when orally administered, can adequately penetrate the blood-brain-barrier of mammals in an amount sufficient to induce $UPR_{mt}$ and mitohormesis in the brain and also prevent the earliest (e.g., presymptomatic) pathogenic subcellular manifestations of a lethal neurodegenerative condition such as Huntington's Disease (HD), and the like.

Accordingly, In various embodiments, the use of N-PPG is contemplated in the treatment and/or prophylaxis of a neurodegenerative disorder in a subject (e.g., a mammal) Illustrative neurodegenerative disorders include, but are not limited to Huntington's disease, Alzheimer's disease, Parkinson's disease, age-related dementia, mild cognitive impairment (MCI), amyotrophic lateral sclerosis (ALS), an ischemic event (e.g., stroke and/or traumatic brain injury), and the like.

Active Ingredient.

It was a surprising discovery, that unlike other inhibitors of PRODH, N-propargylglycine (N-PPG) is capable of activating mitohormesis and is capable of crossing the blood-brain barrier (BBB) in an effective concentration. Accordingly, in various embodiments, methods are provided where N-propargylglycine (N-PPG) is used for the prophylaxis or treatment of a neurological disorder. In certain embodiments, the N-PPG is provided as a mixture of D and L enantiomers. In certain embodiments, the N-PPG is provided as a predominantly L-enantiomer. In certain embodiments, the N-PPG is provided as a predominantly D-enantiomer.

N-propargylglycine (N-PPG) can readily be synthesized using methods well known to those of skill in eth art. Additionally, N-propargylglycine (N-PPG) is commercially available from a number of suppliers (e.g., from BOC Sciences, Shirley, NY).

Indications.

Method are provided that involve the administration of N-PPG for the prophylaxis and/or treatment of a neurodegenerative disorder. Illustrative neurodegenerative disorders include, but are not limited to Huntington's disease, Alzheimer's disease, Parkinson's disease, age-related dementia, mild cognitive impairment (MCI), amyotrophic lateral sclerosis (ALS), an ischemic event (e.g., stroke and/or traumatic brain injury), and the like.

In a prophylactic context, N-PPG is administered in a subject identified as having one or more risk factors for a neurodegenerative disorder, e.g., as described below. Such risk factors can include family history, genetic markers, and/or biochemical markers.

Huntington's Disease.

Huntington's disease (HD) is an autosomal dominant progressive neurodegenerative disorder that typically begins in middle adulthood. The neurodegenerative process that underlies HD, however, likely begins many years before clinical diagnosis. Since genetic testing can identify individuals that will develop HD during this preclinical period, N-PPG finds prophylactic use aiming to slow or stop disease progression. Additionally N-PPG can be used in the treatment of disease after manifestation of symptoms.

Motor abnormalities, including chorea and dystonia, oculomotor dysfunction and gait and balance changes, have been described in HD. Subtle chorea and oculomotor abnormalities appear to be the most commonly detected changes.

Cognitive impairment or dementia is a common feature of symptomatic HD and is perhaps the major cause of functional impairment and disability. The cognitive abnormalities of manifest HD are characterized primarily by executive dysfunction, including problems with planning and organization, flexibility and set shifting and procedural memory and attention. Subclinical abnormalities of cognitive performance can also be detected many years before a clinical diagnosis is determined. The PREDICT-HD study has described impairment across multiple cognitive domains beginning 10-15 years before diagnosis HD severity and/or progression can also be assessed using the Unified Huntington's Disease Rating Scale (UHDRS) (see, e.g., *Huntington study group* (1996) *Movement Disorders,* 11(2): 146-142), which includes four domains that measure motor, cognitive, behavioral and functional status.

In various embodiments, administration of N-PPG is expected to provide improvement in Unified Huntington's disease rating scale (UHDS), motor abnormalities, including chorea and/or dystonia, oculomotor dysfunction, and/or gait and balance changes.

Alzheimer's Disease.

In certain embodiments, the methods described herein (e.g., administration of N-PPG) are believed to be useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, the methods can reduce or eliminate one or more symptoms characteristic of AD and/or delay or prevent the progression from MCI to early or later stage Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's Criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease (AD). McKhann, et al. (1984) *Neurology* 34(7): 939-44. According to these criteria, the presence of cognitive impairment and a suspected dementia syndrome should be confirmed by neuropsychological testing for a clinical diagnosis of possible or probable AD. However, histopathologic confirmation (microscopic examination of brain tissue) is generally used for a dispositive diagnosis. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can be made using classic psychometric measures, such as the Mini-Mental State Exam (MMSE) (Folstein et al. (1975) *J. Psychiatric Research* 12 (3): 189-198), and the Alzheimer's Disease Assessment Scale (ADAS), which is a comprehensive scale for evaluating patients with Alzheimer's Disease status and function (see, e.g., Rosen, et al. (1984) *Am. J.*

*Psychiatr.,* 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al. supra). Any score greater than or equal to 25 points (out of 30) is effectively normal (intact). Below this, scores can indicate severe (<9 points), moderate (10-20 points) or mild (21-24 points) Alzheimer's disease.

Alzheimer's disease can be broken down into various stages including: 1) Moderate cognitive decline (Mild or early-stage Alzheimer's disease), 2) Moderately severe cognitive decline (Moderate or mid-stage Alzheimer's disease), 3) Severe cognitive decline (Moderately severe or mid-stage Alzheimer's disease), and 4) Very severe cognitive decline (Severe or late-stage Alzheimer's disease) as shown in Table 1.

TABLE 1

| Illustrative stages of Alzheimer's disease. |
|---|
| Moderate Cognitive Decline (Mild or early stage AD) |
| At this stage, a careful medical interview detects clear-cut deficiencies in the following areas:<br>Decreased knowledge of recent events.<br>Impaired ability to perform challenging mental arithmetic. For example, to count backward from 100 by 7s.<br>Decreased capacity to perform complex tasks, such as marketing, planning dinner for guests, or paying bills and managing finances.<br>Reduced memory of personal history.<br>The affected individual may seem subdued and withdrawn, especially in socially or mentally challenging situations. |
| Moderately severe cognitive decline (Moderate or mid-stage Alzheimer's disease) |
| Major gaps in memory and deficits in cognitive function emerge. Some assistance with day-to-day activities becomes essential. At this stage, individuals may:<br>Be unable during a medical interview to recall such important details as their current address, their telephone number, or the name of the college or high school from which they graduated.<br>Become confused about where they are or about the date, day of the week or season.<br>Have trouble with less challenging mental arithmetic; for example, counting backward from 40 by 4s or from 20 by 2s.<br>Need help choosing proper clothing for the season or the occasion.<br>Usually retain substantial knowledge about themselves and know their own name and the names of their spouse or children.<br>Usually require no assistance with eating or using the toilet. |
| Severe cognitive decline (Moderately severe or mid-stage Alzheimer's disease) |
| Memory difficulties continue to worsen, significant personality changes may emerge, and affected individuals need extensive help with daily activities. At this stage, individuals may:<br>Lose most awareness of recent experiences and events as well as of their surroundings.<br>Recollect their personal history imperfectly, although they generally recall their own name.<br>Occasionally forget the name of their spouse or primary caregiver but generally can distinguish familiar from unfamiliar faces.<br>Need help getting dressed properly; without supervision, may make such errors as putting pajamas over daytime clothes or shoes on wrong feet.<br>Experience disruption of their normal sleep/waking cycle.<br>Need help with handling details of toileting (flushing toilet, wiping and disposing of tissue properly).<br>Have increasing episodes of urinary or fecal incontinence.<br>Experience significant personality changes and behavioral symptoms, including suspiciousness and delusions (for example, believing that their caregiver is an impostor); hallucinations (seeing or hearing things that are not really there); or compulsive, repetitive behaviors such as hand-wringing or tissue shredding.<br>Tend to wander and become lost. |
| Very severe cognitive decline (Severe or late-stage Alzheimer's disease) |
| This is the final stage of the disease when individuals lose the ability to respond to their environment, the ability to speak, and, ultimately, the ability to control movement.<br>Frequently individuals lose their capacity for recognizable speech, although words or phrases may occasionally be uttered.<br>Individuals need help with eating and toileting and there is general incontinence.<br>Individuals lose the ability to walk without assistance, then the ability to sit without support, the ability to smile, and the ability to hold their head up.<br>Reflexes become abnormal and muscles grow rigid. Swallowing is impaired. |

In various embodiments administration of N-PPG to subjects diagnosed with Alzheimer's disease is deemed effective when there is a reduction in the CSF of levels of one or more components selected from the group consisting of Tau, phospho-Tau (pTau), APPneo, soluble Aβ40, soluble Aβ42, and/or and Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR) of the subject, and/or when the rate of increase in clinical dementia rating is slowed or stopped and/or when the progression of AD is slowed or stopped (e.g., when the transition from one stage to another as listed in Table 3 is slowed or stopped).

In certain embodiments Subjects amenable to the present methods generally are free of a neurological disease or disorder other than Alzheimer's disease. For example, in certain embodiments, the subject does not have and is not at risk of developing a neurological disease or disorder such as Parkinson's disease, and/or schizophrenia, and/or psychosis.

In certain embodiments, N-PPG is administered prophylactically to a subject having one or more risk factors for AD. Such risk factors can include, but are not limited to family history, genetic markers, and/or biochemical markers.

The most common type of Alzheimer's disease usually begins after age 65 (late-onset Alzheimer's disease). The most common gene associated with late-onset Alzheimer's disease is a risk gene called apolipoprotein E4 (APOE4) which increases the risk of Alzheimer's disease. Having one copy of the APOE4 gene increases the risk of developing AD and having two APOE4 genes increases the risk even more.

A very small percentage of people who develop Alzheimer's disease have the early-onset type. Signs and symptoms of this type usually appear between ages 30 and 60 years. This type of Alzheimer's disease has a very strong genetic component. In particular, 3 genes in which mutations cause early-onset Alzheimer's disease include: 1) Amyloid precursor protein (APP); 2) Presenilin 1 (PSEN1); and 3Presenilin 2 (PSEN2).

Mutations of these genes cause the production of excessive amounts of a toxic protein fragment called amyloid-beta peptide. This peptide can build up in the brain to form clumps called amyloid plaques, which are characteristic of Alzheimer's disease. A buildup of toxic amyloid-beta peptide and amyloid plaques may lead to the death of nerve cells and the progressive signs and symptoms of this disorder.

As amyloid plaques collect in the brain, tau proteins malfunction and stick together to form neurofibrillary tangles. These tangles are associated with the abnormal brain functions seen in Alzheimer's disease. Other genes implicated in Alzheimer's disease include, but are not limited to ABCA7, CLU, PLD3, TREM2, and SORL1. CLU helps regulate the clearance of amyloid-beta from the brain. It is believed that an imbalance in the production and clearance of amyloid-beta is central to the development of Alzheimer's disease. A deficiency in the protein produced by CR1 may contribute to chronic inflammation in the brain. Inflammation is another possible factor in the development of Alzheimer's disease. PLD3 has been linked to a significantly increased risk of Alzheimer's disease. TREM2 is involved in the regulation of the brain's response to inflammation. Variants in this gene are associated with an increased risk of Alzheimer's disease. Similarly, variations of SORL1 have been implicated in Alzheimer's disease.

Mild Cognitive Impairment (MCI)

Mild cognitive impairment (MCI, also known as incipient dementia, or isolated memory impairment) is a diagnosis given to individuals who have cognitive impairments beyond that expected for their age and education, but that typically do not interfere significantly with their daily activities (see, e.g., Petersen et al. (1999) *Arch. Neurol.* 56(3): 303-308). It is considered in many instances to be a boundary or transitional stage between normal aging and dementia. Although MCI can present with a variety of symptoms, when memory loss is the predominant symptom it is termed "amnestic MCI" and is frequently seen as a risk factor for Alzheimer's disease (see, e.g., Grundman et al. (2004) *Arch. Neurol.* 61(1): 59-66; and on the internet at en.wikipedia.org/wiki/Mild_cognitive_impairment-cite_note-Grundman-1). When individuals have impairments in domains other than memory it is often classified as non-amnestic single- or multiple-domain MCI and these individuals are believed to be more likely to convert to other dementias (e.g., dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al. (2006) *Arch. Neurol.* 63(5): 665-72).

The diagnosis of MCI typically involves a comprehensive clinical assessment including clinical observation, neuroimaging, blood tests and neuropsychological testing. A similar assessment is usually given for diagnosis of Alzheimer's disease. There is emerging evidence that magnetic resonance imaging can observe deterioration, including progressive loss of gray matter in the brain, from mild cognitive impairment to full-blown Alzheimer disease (see, e.g., Whitwell et al. (2008) *Neurology* 70(7): 512-520). A technique known as PiB PET imaging is used to clearly show the sites and shapes of beta amyloid deposits in living subjects using a C11 tracer that binds selectively to such deposits (see, e.g., Jack et al. (2008) *Brain* 131(Pt 3): 665-680).

Presently, MCI is typically diagnosed when there is 1) Evidence of memory impairment; 2) Preservation of general cognitive and functional abilities; and 3) Absence of diagnosed dementia.

MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The necessary information to make each rating is obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia. An illustrative CDR table is shown in Table 2.

TABLE 2

Illustrative clinical dementia rating (CDR) table.

| | Impairment: | | | | |
|---|---|---|---|---|---|
| | None | Questionable | Mild | Moderate | Severe |
| | CDR: | | | | |
| | 0 | 0.5 | 1 | 2 | 3 |
| Memory | No memory loss or slight inconsistent forgetfulness | Consistent slight forgetfulness; partial recollection of events' "benign" forgetfulness | Moderate memory loss; more marked for recent events; defect interferes with everyday activities | Severe memory loss; only highly learned material retained; new material rapidly lost | Severe memory loss; only fragments remain |
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home<br>Appears well enough to be taken to functions outside a family home | Appears too ill to be taken to functions outside a family home. |
| Home and Hobbies | Life at home, hobbies, and intellectual interests well maintained | Life at home, hobbies, and intellectual interests slightly impaired | Mild bit definite impairment of function at home; more difficult chores abandoned; more complicated hobbies and interests abandoned | Only simple chores preserved; very restricted interests, poorly maintained | No significant function in home |
| Personal Care | Fully capable of self-care | | Needs prompting | Requires assistance in dressing, hygiene, keeping of personal effects | Requires much help with personal care; frequent incontinence |

A CDR rating of −0.5 or −0.5 to 1.0 is often considered clinically relevant MCI. Higher CDR ratings can be indicative of progression into Alzheimer's disease.

In various embodiments administration of N-PPG is deemed effective when there is a reduction in the CSF of levels of one or more components selected from the group consisting of Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR), and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, et al., *Arch Neurol* (2004) 61:59-66 report that a diagnosis of MCI can be established with clinical efficiency using a simple memory test (paragraph recall) to establish an objective memory deficit, a measure of general cognition (Mini-Mental State Exam (MMSE)) to exclude a broader cognitive decline beyond memory, and a structured clinical interview (CDR) with patients and caregivers to verify the patient's memory complaint and memory loss and to ensure that the patient was not demented. Patients with MCI perform, on average, less than 1 standard deviation (SD) below normal on nonmemorycognitive measures included in the battery. Tests of learning, attention, perceptual speed, category fluency, and executive function may be impaired in patients with MCI, but these are far less prominent than the memory deficit.

Parkinson's Disease

Parkinson's disease (PD) has become the second most common neurodegenerative disease following Alzheimer's disease (AD) and is estimated to occur in about 1% of the population over the age of 60 and 4% of the individuals aged over 80 years. The major pathological changes in PD patients are the progressive degeneration of dopaminergic neurons in the substantia nigra and the accumulation of intraneuronal inclusions of the α-synuclein, which are called Lewy bodies. Clinically, PD mainly manifests as motor symptoms, such as bradykinesia, resting tremor, muscle rigidity and postural instability. PD also appears to be correlated with nonmotor symptoms, including olfactory dysfunction, sleep problems, constipation, depression and dysautonomia, due to the neuronal loss in several other brain areas that may occur before or after dopaminergic neurons are lost.

The motor symptoms of bradykinesia, resting tremor and muscle rigidity can be considered as the most significant and direct diagnostic marker for PD. Additionally, these motor features can also be utilized to monitor response to medical treatments and evaluate disease progression in PD. For the early diagnosis of the disease, many non-motor features, including hyposmia, rapid eye movement (REM) sleep behavior disorder, and constipation, are receiving increasing attention as they may be helpful in the detection of prodromal PD.

In various embodiments, it is believed treatment with N-PPG can ameliorate one or more of these symptoms and/or slow the progression of such symptoms.

Amyotrophic Lateral Sclerosis (ALS)

Amyotrophic lateral sclerosis (ALS), is a progressive nervous system disease that affects nerve cells in the brain and spinal cord, causing loss of muscle control. ALS often begins with muscle twitching and weakness in a limb, or slurred speech. Eventually, ALS affects control of the muscles needed to move, speak, eat and breathe. There is no cure for this fatal disease.

In 1993 it was reported that mutations in the gene encoding SOD1 account for about 25% of cases of FALS or 2-3% of all cases. More than 100 different mutations in the SOD1 gene have now been associated with FALS. Forced expression of high levels of a mutant SOD1 transgene causes progressive motor neuron disease in mice and rats. A second ALS gene, the ALS2 has been implicated in ALS. The ALS2 gene codes for a novel protein with homology to guanine-nucleotide exchange factors for GTPases. Loss-of-function of ALS2 leads to denervation beginning in the first decade, with predominant corticobulbar and corticospinal signs and very slow progression. Additionally, it has been observed that a progressive, bulbar-predominant form of lower motor neuropathy arises from mutations in a dynactin gene, suggesting that that motor protein defects can progressively impair motor neuron function, as reported for motor neuropathies from mutations in the kinesin gene.

Signs and symptoms of ALS vary greatly from person to person, depending on which neurons are affected. Signs and symptoms might include, but are not limited to difficulty walking or doing normal daily activities, tripping and falling, weakness in your leg, feet or ankles, hand weakness or clumsiness, slurred speech or trouble swallowing, muscle cramps and twitching in your arms, shoulders and tongue, inappropriate crying, laughing or yawning, and/or cognitive and behavioral changes. ALS often starts in the hands, feet or limbs, and then spreads to other parts of your body. As the disease advances and nerve cells are destroyed, your muscles get weaker. This eventually affects chewing, swallowing, speaking and breathing.

Muscle strength is a clinically relevant measure of disease progression in ALS. There are a variety of methods of varying sophistication available to measure muscle strength. The measures most often used in natural history studies and clinical trials are maximum voluntary isometric contraction (MVIC) and manual muscle testing (MMT).

MVIC has proven useful as an outcome measure in studies and clinical trials in ALS and is a valid and reliable measure of disease progression. MVIC can be measured using a hand-held dynamometer or a fixed device with strain gauges. The strength of individual muscle groups is determined quantitatively and then the scores are normalized and combined into composite scores called megascores. This allows for the averaging of strength of small and large muscle groups.

The MVIC is a good quantitative measure of the rate of decline of muscle strength, an outcome measure that is highly relevant to the disease. The advantages of MVIC include good reliability, sensitivity to small, clinically relevant changes and generation of numerically continuous data which are suitable for parametric statistical analysis.

Another useful technique for evaluating ALS progression uses hand-held dynamometry (HHD) to test isometric strength of multiple muscles, again with standard patient positioning and rigorous training.

Respiratory failure is the primary cause of death in ALS and measurements of respiratory muscle function are commonly used as secondary outcome measures in ALS clinical trials. Vital capacity and maximal inspiratory and maximal expiratory mouth pressures are the methods most commonly used to evaluate respiratory muscle strength. These measures are widely available, non-invasive, and portable. The forced vital capacity (FVC) measures volume of air forcefully expired in one breath. Usually, the FVC is reported as a percentage of a predicted vital capacity based on subject's height, gender and age. The FVC declines with time in patients with ALS and is a sensitive measure of disease progression. Both the baseline FVC and the rate of decline in FVC are predictive of survival. Maximal inspiratory pressure (MIP) measures the maximal negative pressure at the mouth after complete exhalation followed by a single sustained maximal inspiratory effort against an occluded airway. Maximal expiratory pressure (MEP) is the maximal positive pressure measured at the mouth after inhalation to total lung capacity followed by a maximal expiratory effort against an occluded airway. Both MIP and MEP are sensitive early indicators of respiratory muscle weakness.

In various embodiments, treatment with N-PPG is expected to provide a slowing in the progression of, or a reduction in the magnitude of, or an improvement in a symptom of ALS (e.g., an improvement in, a stabilization of, or a reduction in the rate of decline of muscle strength and/or pulmonary function). In certain embodiments, the muscle strength is determined as maximum voluntary isometric contraction. (MVIC), or via hand-held dynamometry (HHD). In certain embodiments, the pulmonary function comprises forced vital capacity (FVC) and/or maximal inspiratory pressure (MIP).

Neurodegeneration Associated with an Ischemic Event.

It has been observed that ischemic events (e.g., stroke, drowning, certain traumatic brain injuries) proceed in two phases: a) An early phase that accompanies or immediately follows the ischemic event itself; and 2) A secondary phase that occurs from about 48 hours up to 6 or 10 days following the initial ischemic event.

It is believe that in various embodiments, the administration of N-PPG can improve, a stabilization or reduce the amount and/or rate of neurological damage following an ischemic event.

Pharmaceutical Formulations and Administration

Pharmaceutical Formulations.

N-propargylglycine (N-PPG) administered in any of the therapies described above will typically be formulated according standard practice. In some embodiments, a pharmaceutical formulation including N-PPG and a pharmaceutically acceptable carrier is provided.

In various embodiments, the N-PPG can be administered in the "native" form or, if desired, in the form of salts, esters, amides, prodrugs, derivatives, and the like, provided the salt, ester, amide, prodrug, or derivative is suitable pharmacologically, i.e., effective in the present method. Salts, esters, amides, prodrugs, and other derivatives of N-PPG can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Pharmaceutically acceptable salts include those derived from pharmaceutically acceptable, inorganic and organic acids and bases. Examples of suitable acids include hydrochloric, hydrobromic, sulfuric, nitric, perchloric, fumaric, maleic, phosphoric, glycollic, lactic, salicyclic, succinic, gluconic, isethionic, glycinic, malic, mucoic, glutammic, sulphamic, ascorbic acid; toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include but are not limited to alkali such as sodium and ammonium.

For example, acid addition salts are prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Illustrative acid addition salts are halide salts, such as may be prepared using hydrochloric or hydrobromic acids. Conversely, basic salts of are prepared in a similar manner using a pharmaceutically acceptable base such as sodium hydroxide, potassium hydroxide, ammonium hydroxide, calcium hydroxide, trimethylamine, or the like. Illustrative basic salts include alkali metal salts, e.g., the sodium salt, and copper salts.

Acid addition salts useful in the methods described herein include the physiologically compatible acid addition salts, most preferably the dihydrochloride. Bis-quaternary salts useful in the methods described herein include the physiologically compatible bis-quaternary salts, such as the methiodide and the dimethiodide.

Preparation of esters typically involves functionalization of hydroxyl and/or carboxyl groups and/or other reactive groups that may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

N-PPG can be combined with a pharmaceutically acceptable carrier (excipient), such as are described in Remington's Pharmaceutical Sciences (1980) 16th editions, Osol, ed., 1980. Pharmaceutically acceptable carriers can contain one or more physiologically acceptable compound(s) that act, for example, to stabilize the composition or to increase or decrease the absorption of the active agent (N-PPG). A pharmaceutically acceptable carrier suitable for use in the methods described herein is non-toxic to cells, tissues, or subjects at the dosages employed, and can include a buffer (such as a phosphate buffer, citrate buffer, and buffers made from other organic acids), an antioxidant (e.g., ascorbic acid), a low-molecular weight (less than about 10 residues) peptide, a polypeptide (such as serum albumin, gelatin, and an immunoglobulin), a hydrophilic polymer (such as polyvinylpyrrolidone), an amino acid (such as glycine, glutamine, asparagine, arginine, and/or lysine), a monosaccharide, a disaccharide, and/or other carbohydrates (including glucose, mannose, and dextrins), a chelating agent (e.g., ethylenediaminetetratacetic acid (EDTA)), a sugar alcohol (such as mannitol and sorbitol), a salt-forming counterion (e.g., sodium), and/or an anionic surfactant (such as TWEEN™, PLURONICS™, and PEG). In one embodiment, the pharmaceutically acceptable carrier is an aqueous pH-buffered solution.

Other pharmaceutically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration N-PPG and on the particular physio-chemical characteristics of this compound.

Pharmaceutical formulations described herein can be stored in any standard form, including, e.g., an aqueous solution or a lyophilized cake. Such compositions are typically sterile when administered to subjects. Sterilization of an aqueous solution is readily accomplished by filtration through a sterile filtration membrane. If the composition is stored in lyophilized form, the composition can be filtered before or after lyophilization and reconstitution.

N-PPG can exist in different stereoisomeric forms including enantiomers of (+) and (−) type or mixtures of them. In various embodiments, the use of either the individual isomers or the mixtures thereof is contemplated herein.

It will be understood that, when mixtures of optical isomers are present, they may be separated according to the classic resolution methods based on their different physicochemical properties, e.g., by fractional crystallization of their acid addition salts with a suitable optically active acid or by the chromatographic separation with a suitable mixture of solvents.

Administration

The N-PPG can be administered by any convenient route of administration. In various embodiments, N-PPG can be administered by intravenous, intraarterial, intrathecal, intradermal, intracavitary, oral, rectal, intramuscular, subcutaneous, intracisternal, intravaginal, intraperitonial, topical, buccal, and/or nasal routes of administration. In various embodiments, the N-PPG can be administered orally, in which case delivery can be enhanced by the use of protective excipients. This is typically accomplished either by complexing the N-PPG with a composition to render it resistant to acidic and enzymatic hydrolysis or by packaging the N-PPG in an appropriately resistant carrier. Means of protecting agents for oral delivery are well known in the art (see, e.g., U.S. Pat. No. 5,391,377).

Elevated serum half-life can be maintained by the use of sustained-release "packaging" systems. Such sustained release systems are well known to those of skill in the art (see, e.g., Tracy (1998) *Biotechnol. Prog.* 14: 108; Johnson et al. (1996), *Nature Med.* 2: 795; Herbert et al. (1998), *Pharmaceut. Res.* 15, 357).

Suitable pharmaceutical formulations can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc. In another embodiment, one or more components of a solution can be provided as a "concentrate," e.g., in a storage container (e.g., in a premeasured volume) ready for dilution or in a soluble capsule ready for addition to a volume of water.

In certain embodiments, the N-PPG may also be delivered through the skin using conventional transdermal drug delivery systems, i.e., transdermal "patches" wherein the N-PPG is contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir or may take some other form. The backing layer in these laminates, which serves as the upper surface of the device, preferably functions as a primary structural element of the "patch" and provides the device with much of its flexibility. The material selected for the backing layer is preferably substantially impermeable to the N-PPG and any other materials that are present.

In certain embodiments, the N-PPG is administered alone or in combination with other therapeutics in implantable (e.g., subcutaneous) matrices, termed "depot formulations."

A major problem with standard drug dosing is that typical delivery of drugs results in a quick burst of medication at the time of dosing, followed by a rapid loss of the drug from the body. Most of the side effects of a drug occur during the burst phase of its release into the bloodstream. Secondly, the time the drug is in the bloodstream at therapeutic levels is very short; most is used and cleared during the short burst.

Drugs (e.g., N-PPG) imbedded in various matrix materials for sustained release can mitigate these problems. Drugs embedded, for example, in polymer beads or in polymer wafers have several advantages. First, most systems allow slow release of the drug, thus creating a continuous dosing of the body with small levels of drug. This typically prevents side effects associated with high burst levels of normal injected or pill-based drugs. Secondly, since these polymers can be made to release over hours to months, the therapeutic span of the drug is markedly increased. Often, by mixing different ratios of the same polymer components, polymers of different degradation rates can be made, allowing remarkable flexibilit. A long rate of drug release is beneficial for people who might have trouble staying on regular dosage, such as the elderly, but also represents an ease of use improvement that everyone can appreciate. Most polymers can be made to degrade and be cleared by the body over time, so they will not remain in the body after the therapeutic interval.

Another advantage of polymer-based drug delivery is that the polymers often can stabilize or solubilize proteins, peptides, and other large molecules that would otherwise be unusable as medications. Finally, many drug/polymer mixes can be placed directly in the disease area, allowing specific targeting of the medication where it is needed without losing drug to the "first pass" effect. This is certainly effective for treating the brain, which is often deprived of medicines that can't penetrate the blood/brain barrier.

A wide variety of approaches to designing depot formulations that can provide sustained release of N-PPG are known and are suitable for use in the methods described herein. Generally, the components of such formulations are biocompatible and may be biodegradable. Biocompatible polymeric materials have been used extensively in therapeutic drug delivery and medical implant applications to effect a localized and sustained release (see, e.g., Leong et al. (1987) *Adv. Drug Deliv. Rev.,* 1:199-233; Langer (1990) *Science,* 249: 1527-1533; and the like). Such delivery systems offer the potential of enhanced therapeutic efficacy and reduced overall toxicity.

Examples of classes of synthetic polymers that have been studied as possible solid biodegradable materials include polyesters (Pitt et al., "Biodegradable Drug Delivery Systems Based on Aliphatic Polyesters: Applications to Contraceptives and Narcotic Antagonists," Controlled Release of Bioactive Materials, 19-44 (Richard Baker ed. (1980); Poly(amino acids) and pseudo-poly(amino acids) (Pulapura et al. (1992) *J. Biomaterials Appl.,* 6(1): 216-250); polyurethanes (Bruin et al. (1990) *Biomaterials,* 11(4): 291-295); polyorthoesters (Heller et al. (1981) *Polymer Engineering Sci.,* 21(11): 727-731); and polyanhydrides (Leong et al. (1986) *Biomaterials* 7(5): 364-371).

Thus, for example, N-PPG can be incorporated into a biocompatible polymeric composition and formed into the desired shape outside the body. This solid implant is then typically inserted into the body of the subject through an incision. Alternatively, small discrete particles composed of these polymeric compositions can be injected into the body, e.g., using a syringe. In an illustrative embodiment, N-PPG can be encapsulated in microspheres of poly (D,L-lactide) polymer suspended in a diluent of water, mannitol, carboxymethyl-cellulose, and polysorbate 80. The polylactide polymer is gradually metabolized to carbon dioxide and water, releasing the N-PPG into the system.

In yet another approach, depot formulations can be injected via syringe as a liquid polymeric composition. Liquid polymeric compositions useful for biodegradable controlled release drug delivery systems are described, e.g., in U.S. Pat. Nos. 4,938,763; 5,744,153; 5,990,194; and 5,324,519. After injection in a liquid state or, alternatively, as a solution, the composition coagulates into a solid.

One type of polymeric composition suitable for this application includes a nonreactive thermoplastic polymer or copolymer dissolved in a body fluid-dispersible solvent. This polymeric solution is placed into the body where the polymer congeals or precipitates and solidifies upon the dissipation or diffusion of the solvent into the surrounding body tissues. See, e.g., Dunn et al., U.S. Pat. Nos. 5,278,201; 5,278,202; and 5,340,849 (disclosing a thermoplastic drug delivery system in which a solid, linear-chain, biodegradable polymer or copolymer is dissolved in a solvent to form a liquid solution).

In certain embodiments the N-PPG can also be adsorbed onto a membrane, such as a silastic membrane, which can be implanted, as described in International Publication No. WO 91/04014. Other illustrative implantable sustained release systems include, but are not limited to Re-Gel®, SQ2Gel®, and Oligosphere® by MacroMed, ProLease® and Medisorb® by Alkermes, Paclimer® and Gliadel® Wafer by Guilford pharmaceuticals, the Duros implant by Alza, acoustic biSpheres by Point Biomedical, the Intelsite capsule by Scintipharma, Inc., and the like.

Dose

In therapeutic applications, the N-PPG is administered to a subject in an amount sufficient to reduce, and/or delay, and or stop, and/or reverse neurodegeneration. Amounts effective for this use may depend upon disease status, the degree of improvement sought, and the general state of the subject's health. Single or multiple administrations of N-PPG may be administered depending on the dosage and frequency as required and tolerated by the subject.

The dose of N-PPG can vary widely and will be selected primarily based on fluid volumes, viscosities, body weight and the like in accordance with the particular mode of administration selected and the subject's needs. In accordance with standard practice, the clinician can titer the dosage and modify the route of administration as required to obtain the optimal therapeutic effect. Generally, the clinician begins with a low dose and increases the dosage until the desired therapeutic effect is achieved. Starting doses can, for example be extrapolated from in vitro and/or animal data.

It was surprisingly discovered that a dose of N-PPG that is effective to induce mitohormesis is low enough that adverse effects associated with inhibition of PRODH are substantially mitigated or eliminated. Without being bound to a particular theory, it is believed an effective dosage for the treatment and/or prophylaxis of a neurodegenerative disorder ranges from about 25 mg/kg up to about 400 mg/kg, or up to about 300 mg/kg. In certain embodiments it is believed an effective dosage for the treatment and/or prophylaxis of a neurodegenerative disorder ranges from about 50/mg/kg up to about 200 mg/kg.

Kits.

In certain embodiments, kits are provided containing N-PPG for the practice of any of the methods described herein. In certain embodiments the kit comprises a container containing a N-PPG, e.g., a container containing one or more unit dosage forms of N-PPG.

Additionally, in certain embodiments, the kits can include instructional materials disclosing the use of N-PPG in the treatment and/or prophylaxis of a neurodegenerative disorder as described herein.

In addition, the kits optionally include labeling and/or instructional materials providing directions (e.g., protocols) for the use of N-PPG. Instructional materials can also include recommended dosages, description(s) of counter-indications, and the like.

While the instructional materials in the various kits typically comprise written or printed materials they are not limited to such. Any medium capable of storing such instructions and communicating them to an end user is contemplated by this invention. Such media include but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Evaluation of N-Propargylglycine (N-PPG) for the Treatment or Prophylaxis of Neurodegenerative Disorders Experimental Design and Methods.

To demonstrate that N-PPG treatment can adequately penetrate the blood-brain-barrier of mammals sufficient to induce $UPR_{mt}$ and mitohormesis in the brain and also prevent the earliest (presymptomatic) proteotoxic subcellular manifestations of a lethal neurodegenerative condition like Huntington's Disease (HD), we conducted a single large in vivo mouse experiment to address two related study questions: 1) Study A was conducted to determine if in normal/wildtype (W) mice of B6/CBA background, there is dose-dependent brain penetration of orally administered N-PPG sufficient to activate brain $UPR_{mt}$ and stimulate normal brain neuronal cell functions; and 2) Study B was conducted using an established genetically engineered HD-like mouse model (Htt-mut, R6/2 in B6/CBA background) to determine if there molecular evidence of normalization of the subcellular pathogenetic brain mechanisms associated with and preceding the inevitable HD-related death of Htt-mut mice (prior to age 20 weeks) if they are treated early and repetitively for up to 9 days and before onset of any neurologic symptoms using a N-PPG dose sufficient to activate $UPR_{mt}$.

For Study A, beginning at 5 weeks of age, seven male and female mice (WT) were daily administered oral N-PPG over a graduated dose range of 50 mg/kg to 200 mg/kg for 9 days, while 4 other age- and sex-matched control mice (W) were given only daily saline.

For Study B, beginning at 5-weeks of age, four male and female Htt-mut mice (HT) were administered oral N-PPG at 50 mg/kg daily for 9 days, while four other age- and sex-matched Htt-mut mice (H) were given only daily saline. All Study A and B mice were sacrificed within 4 h of receiving their last treatment (week 7). By the time of sacrifice and based on repeated body weight and vitality measurements, all mice appeared healthy and asymptomatic. Excised brains were snap frozen in liquid nitrogen for latter cryopulverization, extraction and analysis of total brain RNA and protein.

Experimental Results.

Study A and B protein and RNA expression results are shown in the attached Figures, confirming the following summary of results:

Study A. In normal WT treated mice as compared to normal W control (saline treated) mice, daily treatments of 50, 100, 150 and 200 mg/kg N-PPG produced a dose-dependent 40% to 60% decline in brain mitochondrial PRODH protein levels, with change in PRODH mRNA and without any systemic or neurologic side effects. PRODH protein decline following the 50 mg/kg dose was consistently and concordantly associated with increased mitochondrial YME1L1 mRNA and protein expression, signaling the induction of mouse brain $UPR_{mt}$ and mitohormesis. Whole brain transcriptome (RNAseq) and pathway analyses demonstrated significant (FDR $p<0.05$) N-PPG upregulation of pathways (GO, Reactome) specifically regulating neuronal cell functions including pre- and post-synaptic transmission components and neurotransmitting receptors, primarily involving glutamatergic and GABA-ergic synapses and signaling, and secondarily involving specific voltage-gated ion channel pathways.

Study B. In N-PPG treated Htt-mut mice (HT, 50 mg/kg/day orally×9 days), relative to untreated Htt-mut mice (H, saline only), whole brain protein analysis confirmed $UPR_{mt}$ induction by N-PPG (partial mitochondrial PRODH protein degradation) comparable to that seen in Study A WT mice; as well, whole brain RNA transcriptome (RNAseq) analysis demonstrated partial-to complete normalization by N-PPG of the massively deranged whole brain transcriptomes of age- and sex-matched untreated Htt-mut mice, including specific genes associated with neurodegeneration (TH, DRD1, ADORA2A), and full transcriptome normalization in one of the four Htt-mut treated mice.

CONCLUSIONS

The above two-part in vivo mouse study conclusively demonstrates that, for the first time, a systemically well tolerated antimitochondrial suicide/irreversible inhibitor of PRODH, N-PPG, when administered orally and repeatedly, is capable of crossing the mammalian blood-brain-barrier sufficient to induce brain cell $UPR_{mt}$ and mitohormesis, without causing any adverse systemic or neurologic consequences and, instead, producing potentially beneficial stimulatory effects on normal global brain function and pathways. Most impressively, this well tolerated oral dose of N-PPG can significantly reverse/prevent the massively deranged gene expression features that predate and manifest the subcellular pathogenic mechanisms and lethal brain consequences common to various neurodegenerative disease like Huntington's.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for the treatment and/or prophylaxis of a neurodegenerative disorder in need thereof, said method comprising:

administering to a mammal identified as having or as at risk for said neurodegenerative disorder an effective amount of N-propargylglycine (N-PPG), wherein the disorder is selected from the group consisting of Huntington's disease, Alzheimer's disease, Parkinson's disease, age-related dementia, mild cognitive impairment (MCI), amyotrophic lateral sclerosis (ALS), and an ischemic event.

2. The method of claim 1, wherein said method is for the prophylaxis of said neurodegenerative disorder.

3. The method of claim 2, wherein said mammal is a mammal identified as being at elevated risk for said neurodegenerative disorder.

4. The method of claim 3, wherein said mammal has a marker for said neurodegenerative disorder.

5. The method of claim 4, wherein said neurodegenerative disorder comprises Alzheimer's disease and said marker comprises a marker selected from the group consisting of an ApoE4 allele, a CLR1 gene, and a PLD3 gene, a TREM2 variant, and a SORL1 variant.

6. The method of claim 4, wherein said neurodegenerative disorder comprises Alzheimer's disease and said marker comprises a marker selected from the group consisting of a mutant amyloid precursor protein (APP) gene, a mutant presenilin 1 (PSEN1) gene, and a mutant presenilin 2 (PSEN2) gene.

7. The method of claim 4, wherein said neurodegenerative disorder comprises Huntington's disease and said marker comprises CAG repeats in the Huntington gene.

8. The method of claim 1, wherein said method is for the treatment of said neurodegenerative disorder.

9. The method of claim 2, wherein said neurodegenerative disorder comprises Huntington's disease.

10. The method of claim 9, wherein said method provides a slowing in the progression of, or a reduction in the magnitude of, or an improvement of a symptom of Huntington's disease.

11. The method of claim 10, wherein said method provides a slowing in the progression of, or a reduction in the magnitude of, or an improvement of an indication selected from the group consisting of a Unified Huntington's disease rating scale (UHDS), a motor abnormalities including chorea and/or dystonia, an oculomotor dysfunction, and a problem with gait and balance.

12. The method of claim 2, wherein said neurodegenerative disorder comprises Parkinson's disease.

13. The method of claim 12, wherein said method provides a slowing in the progression of, or a reduction in the magnitude of, or an improvement of a symptom of Parkinson's disease.

14. The method of claim 10, wherein said method provides a slowing in the progression of, or a reduction in the magnitude of, or an improvement of a symptom selected from the group consisting of bradykinesia, resting tremor, and muscle rigidity.

15. The method of claim 2, wherein said neurodegenerative disorder comprises Alzheimer's disease.

16. The method of claim 15, wherein said method provides a slowing in the progression of, or a reduction in the magnitude of, or an improvement in a symptom of Alzheimer's disease.

17. The method of claim 16, wherein said method provides a reduction in the CSF of levels of one or more components selected from the group consisting of Aβ42, sAPPβ, total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, and sAPPα/Aβ42 ratio.

18. The method of claim 17, wherein said administration produces a reduction of the plaque load in the brain of the subject.

19. The method of claim 17, wherein said administration produces a reduction in the rate of plaque formation in the brain of the subject.

20. The method of claim 17, wherein said administration produces an improvement in the cognitive abilities of the subject.

21. The method of claim 17, wherein said administration produces an improvement in, a stabilization of, or a reduction in the rate of decline of the clinical dementia rating (CDR) of the subject.

22. The method of claim 2, wherein said neurodegenerative disorder comprises age-related dementia and/or mild cognitive impairment (MCI).

23. The method of claim 22, wherein said method provides a slowing in the progression of, or a reduction in the magnitude of, or an improvement in a symptom of age-related dementia and/or mild cognitive impairment (MCI).

24. The method of claim 23, wherein said method provides an improvement in, a stabilization of, or a reduction in the rate of decline of the clinical dementia rating (CDR) of the subject.

25. The method of claim 2, wherein said neurodegenerative disorder comprises amyotrophic lateral sclerosis (ALS).

26. The method of claim 25, wherein said method provides a slowing in the progression of, or a reduction in the magnitude of, or an improvement in a symptom of ALS.

27. The method of claim 26, wherein said method provides an improvement in, a stabilization of, or a reduction in the rate of decline of muscle strength and/or pulmonary function.

28. The method of claim 27, wherein said muscle strength is determined as maximum voluntary isometric contraction, (MVIC), or via hand-held dynamometry (HHD).

29. The method of claim 27, wherein said pulmonary function comprises forced vital capacity (FVC) and/or maximal inspiratory pressure (MIP).

30. The method of claim 2, wherein said neurodegenerative disorder comprises delayed neurodegeneration following an ischemic event.

31. The method of claim 30, wherein said ischemic event is due to stroke or traumatic brain injury.

32. The method of claim 31, wherein said method provides an improvement in, a stabilization of, or a reduction in the rate of neurological damage.

33. The method of claim 1, wherein said administering causes specific degradation of mitochondrial PRODH protein.

34. The method of claim 1, wherein said administering produce an increase in YMEIL1.

35. The method of claim 1, wherein said administering upregulates expression of one or more of DRD1, TH, or ADORA to normal levels seen in a wildtype mammal without a neurodegenerative disorder.

36. The method of claim 1, wherein said administering is at a dosage that produces no adverse side effects associated with downregulation or inhibition of PRODH.

37. The method of claim 1, wherein said administering is at a dose that ranges from about 50 mg/kg up to about 200 mg/kg.

38. The method of claim 1, wherein said administering has substantially no effect on monoamine oxidase B levels.

39. The method of claim 1, wherein said administering has substantially no effect on monoamine oxidase A levels.

40. The method of claim 1, wherein said administering has substantially no effect on monoamine oxidase levels.

41. The method of claim 1, wherein said mammal is a human.

42. The method of claim 1, wherein said mammal is a non-human mammal.

43. The method of claim 1, wherein said N-PPG is administered to said mammal for at least one month, at least two months, at least 3 months, at least 4 months, at least 5 months, at least 6 months, or at least 1 year.

44. The method of claim 1, wherein said N-PPG is an oral formulation that is administered at least once daily.

45. The method of claim 1, wherein said N-PPG is an oral formulation that is administered at least once daily.

46. The method of claim 1, wherein said mammal is not diagnosed with and/or under treatment for a cancer.

* * * * *